US00PP11043P

United States Patent [19]

Churchus

[11] Patent Number: Plant 11,043

[45] Date of Patent: Aug. 24, 1999

[54] LOBELIA PLANT NAMED 'TRUE BLUE'

[75] Inventor: John William Churchus, Devon Meadows, Australia

[73] Assignee: Plants Management Australia Pty. Ltd., Warragul, Australia

[21] Appl. No.: 09/019,027

[22] Filed: Feb. 5, 1998

[51] Int. Cl.[6] ..... A01H 5/00

[52] U.S. Cl. ..... Plt./263

[58] Field of Search ..... Plt./263

[56] References Cited

U.S. PATENT DOCUMENTS

P.P. 10,758 1/1999 Westhoff ..... Plt./263

OTHER PUBLICATIONS

UPOV–ROM Citation for ( True Blue) as per NZ PBR HOMO52, Jul. 5, 1995.

UPOV ROM Citation for (True Blue) as per JP PBR 5406, Aug. 7, 1992.

*Primary Examiner*—Howard J. Locker
*Assistant Examiner*—Kent L. Bell
*Attorney, Agent, or Firm*—C. A. Whealy

[57] ABSTRACT

A new and distinct cultivar of Lobelia plant named 'True Blue', characterized by its compact and prostrate spreading plant habit; purplish green stems; numerous lavender flowers; long flowering period; tolerance to high and low temperatures; and resistance to fungal pathogens common to Lobelia.

1 Drawing Sheet

BACKGROUND OF THE INVENTION

The present invention relates to a new and distinct cultivar of Lobelia plant, botanically known as *Lobelia erinus*, and hereinafter referred to by the cultivar name 'True Blue'.

The new cultivar was discovered by the inventor in Devon Meadows, Victoria, Australia, as a naturally-occuring mutation of the nonpatented *Lobelia erinus* 'Minstral' and was observed in a group of plants of the parent cultivar in 1994.

Asexual reproduction of the new cultivar by terminal cuttings taken at Devon Meadows, Victoria, Australia, has shown that the unique features of this new Lobelia are stable and reproduced true to type in successive generations of asexual reproduction.

BRIEF SUMMARY OF THE INVENTION

The following traits have been repeatedly observed and are determined to be the unique characteristics of 'True Blue'. These characteristics in combination distinguish the new Lobelia as a new and distinct cultivar:

1. Compact and prostrate spreading plant habit.
2. Purplish green stems.
3. Numerous lavender flowers.
4. Long flowering period.
5. Tolerance to high and low temperatures.
6. Resistance to fungal pathogens common to Lobelia.

Compared to plants of the parent cultivar, *Lobelia erinus* 'Minstral', plants of the new Lobelia are more compact, more prostrate, denser, and leaves and stems are more pubescent.

The new Lobelia has not been observed under all possible environmental conditions. The phenotype may vary significantly with variations in environment such as temperature and light level, without, however, any variance in genotype.

BRIEF DESCRIPTION OF THE PHOTOGRAPHS

The accompanying colored photographs illustrate the overall appearance and flower color of the new Lobelia, showing the colors as true as it is reasonably possible to obtain in colored reproductions of this type.

The photograph at the top of the sheet comprises a side perspective view of a typical plant of the new Lobelia.

The photograph at the bottom of the sheet comprises a close-up view of a typical flower of the new Lobelia. Flower and foliage colors in the photographs may appear different from the actual colors due to light reflectance. In this regard, the photograph at the bottom of the sheet illustrates a more lavender bloom coloration.

DETAILED BOTANICAL DESCRIPTION

The following observations, measurements, values, and comparisons describe plants grown under outdoor production conditions in 16.5-cm containers in Keller, Tex., in partial shade during the summer.

In the following description, color references are made to The Royal Horticultural Society Colour Chart except where general terms of ordinary dictionary significance are used.

Botanical classification: *Lobelia erinus* cultivar 'True Blue'.

Parentage: Naturally-occuring mutation of *Lobelia erinus* cultivar 'Minstral' (not patented).

Propagation:

*Method.*—By terminal cuttings or by tissue culture.

*Time to initiate roots.*—Summer: About 5 days at a temperature of 25°C. Winter: About 7 days at a temperature of 15°C.

*Time to develop roots.*—Summer: About 15 days at a temperature of 25°C. Winter: About 25 days at a temperature of 15°C.

*Rooting habit.*—Numerous, fibrous, and freely-branching.

Plant description:

*Form.*—Low-growing, prostrate, spreading to cascading herbaceous perennial. Freely branching, dense and bushy growth. Numerous lavender flowers that face outward.

*Usage.*—Suitable for 10 to 25-cm containers; recommended for hanging baskets and patio containers; excellent garden performance. Tolerant to low and high temperatures.

*Vigor.*—Moderate and moderate growth rate.

*Plant height.*—About 10 cm.

*Plant spread.*—About 55 cm.

*Branching habit.*—Freely branching with lateral branches forming at every node, pinching will enhance branching, branches very strong and flexible.

*Stem description.*—Lateral branch diameter: About 1.5 mm. Internode length: About 1.25 cm. Texture: Sparsely pubescent. Color: Green, 145A, with reddish purple tones. New growth purple, 79A.

*Foliage description.*—Leaves simple, generally symmetrical, abundant, alternate and flat in aspect. Length: About 2 cm. Width: About 1.8 cm. Shape: Broadly ovate with rounded apex, obtuse to attenuate base and crenate margin. Texture: Sparsely pubescent, glossy. Color: Young leaves, upper surface: 147A. Young leaves, lower surface: 79A. Fully expanded leaves, upper surface: 147A. Fully expanded leaves, lower surface: Close to 146A with purple tones, glossier than upper surface. Petiole: Length: About 1.25 cm. Diameter: About 1.5 mm. Color: 147B with purple, 79A, tones.

Flower description:

*Flower type and habit.*—Flowers form at apical axils. Usually one flower per axil. Flowers labiate, upper lip consisting of two small petals; and lower lip consisting of three larger and broader petals. Petals fused at base into a tube. Freely and continuously flowering. Flowers face outward. Flowers persistant.

*Flowering season.*—Flowering generally occurs spring throughout summer. Vegetative growth continues throughout flowering period.

*Flower width.*—About 1.25 cm.

*Flower length.*—About 1.3 cm.

*Flower depth.*—About 1.5 cm.

*Flower buds.*—Length: About 8 mm. Diameter: About 2 mm. Shape: Tubular. Color: Light green.

*Petals.*—Length: Upper petals: About 5 mm. Lower petals: About 6.5 mm. Width: Upper petals: About 1 mm. Lower petals: About 4 mm. Shape: Upper petals: Linear with acute apex and entire margin. Lower petals: Oblong with acute apex and entire margin. Texture: Sparsely pubescent towards tube, upper petals more pubescent. Throat, whiskered. Color: When opening, upper surface: 91A. Mature, upper surface: 91A, white at base. Petals may fade to 91B with subsequent development. Mature, lower surface: 91B. Tube, upper surface: 91A. Tube, lower surface: 91B. Throat: White background with three dark blue, close to 89A, spots and two yellow stripes.

*Sepals.*—Arrangement: Five fused at base, star-shaped. Shape: Very narrowly linear with acute apex and entire margin. Calyx length: About 7.5 mm. Calyx diameter at base: About 2 mm. Texture: Smooth. Color: 144A where fused to 147A towards apex.

*Peduncles.*—Length: About 1.5 cm. Angle: Upright. Strength: Wiry, flexible. Color: 146A.

*Reproductive organs.*—Androecium: Stamen number: Five. Anther shape: Oblong. Anther length: About 1 mm. Anther color: Dark purple. Amount of pollen: Moderate. Pollen color: Whitish. Gynoecium: Pistil length: About 1 cm. Stigma shape: Bilobate. Stigma color: Purple. Style color: Green. Ovary color: Green.

Seed development: Seed development has not been observed on plants of the new Lobelia.

Disease resistance: Under commercial conditions, plants of the new Lobelia are resistant to fungal pathogens common to Lobelia.

It is claimed:

1. A new and distinct Lobelia plant named 'True Blue', as illustrated and described.

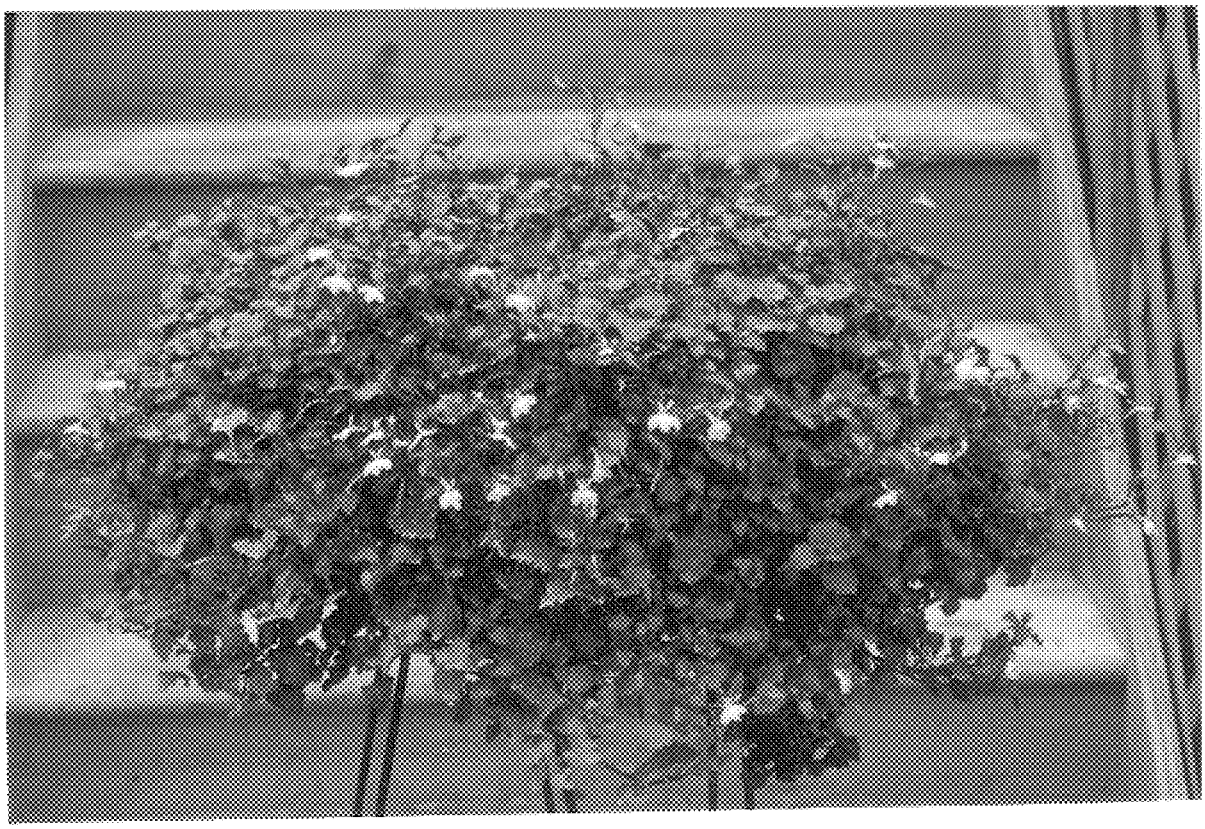
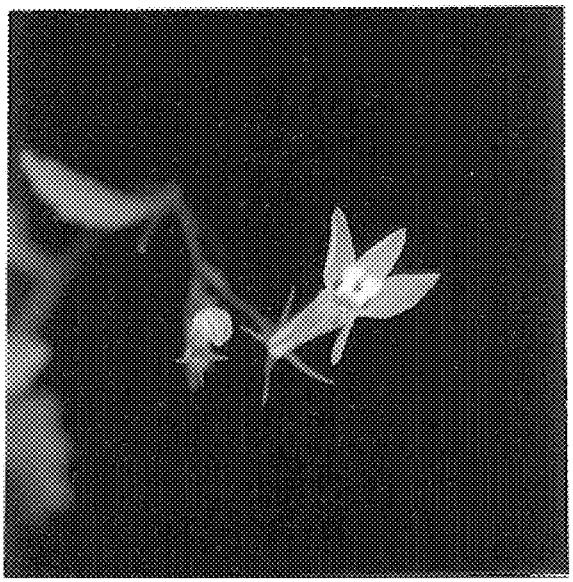

* * * * *